United States Patent [19]
Goodin et al.

[11] Patent Number: 5,791,036
[45] Date of Patent: Aug. 11, 1998

[54] CATHETER TRANSITION SYSTEM

[75] Inventors: Richard L. Goodin, Blaine; Richard S. Kusleika, Eden Prairie; Kathy M. Prindle, Robbinsdale; Mary S. Bronson, Elk River; Kristen L. Swanson, St. Paul, all of Minn.

[73] Assignee: Schneider (USA) Inc, Minneapolis, Minn.

[21] Appl. No.: 772,324

[22] Filed: Dec. 23, 1996

[51] Int. Cl.[6] .......................... B23P 17/00; B29C 65/00
[52] U.S. Cl. .............................. 29/423; 604/280
[58] Field of Search ................. 29/423, 428, 525.01, 29/516; 604/280, 282, 283; 128/658; 285/235, 292, 381, 417, 423; 600/435

[56] References Cited

U.S. PATENT DOCUMENTS

| | | | |
|---|---|---|---|
| 5,178,158 | 1/1993 | De Toledo | 604/280 |
| 5,308,342 | 5/1994 | Sepetka et al. | 604/282 |
| 5,445,624 | 8/1995 | Jimenez | 604/280 |
| 5,496,294 | 3/1996 | Hergenrother et al. | 604/282 |
| 5,499,973 | 3/1996 | Saab . | |
| 5,569,218 | 10/1996 | Berg | 604/280 X |
| 5,569,220 | 10/1996 | Webster et al. | 604/282 |
| 5,569,221 | 10/1996 | Houser et al. | 604/282 |
| 5,676,659 | 10/1997 | McGurk | 604/282 |
| 5,700,252 | 12/1997 | Klingenstein | 604/280 |
| 5,702,373 | 12/1997 | Samson | 604/280 X |

Primary Examiner—S. Thomas Hughes
Attorney, Agent, or Firm—Haugen and Nikolai, P.A.; Philip C. Strassburger, Esq.

[57] ABSTRACT

A method of joining successive sections of tubular members having substantially dissimilar flexibilities is involved that includes the step of providing a transitional zone intermediate said successive sections having a flexibility intermediate those of the successive sections. Articles made by the process are also disclosed.

10 Claims, 8 Drawing Sheets

CATHETER TRANSITION SYSTEM

BACKGROUND OF THE INVENTION

I. Field of the Invention

The present invention relates to vascular catheters, and particularly, to vascular catheters characterized by elongated multi-lumenal shafts carrying distal devices dedicated to perform particular procedures in remote vessels such as balloon dilatation catheters. More specifically, this invention relates to improvements in the construction of the catheter tubes themselves with regard to joining catheter tube sections having different physical properties such as hardnesses, flexibilities and torquing qualities.

II. Related Art

Contemporary balloon dilatation catheter construction often requires mating a long, relatively stiff proximal shaft with a shorter, relatively flexible distal stem section which carries the dilatation device. The proximal shaft is employed to negotiate the arterial system of a patient and requires a certain minimum stiffness for proper or ease of vascular navigation and negotiation. Torqueability is not a particular requirement for the proximal shaft portion of the catheter. Typically, the outer wall of the shaft assumes a round or nearly round cross section and is fashioned of layers of low friction polymer material applied over or surrounding a braided or coil core. The density and stiffness of the material making up the braided or coil core further helps in defining the stiffness of the shaft. The shaft is typically polyimide, polyamide, polyolefin or other material having a nominal hardness of 72–80 Durometer (D Shore Scale). The braid or coil core is normally woven from small diameter stainless steel filament material. The shaft tube may be made as a composite structure of several layers. One or more inner layers of a polymer material may be sprayed on a mandrel of the desired configuration and size, the reinforcing braid or coil applied over the inner layer and one or more additional layers of polymer material may be sprayed over the braid or coil. The shaft tube may also be made by co-extrusion techniques.

The flexible distal tubular stem section is relatively shorter and carries the dilatation device. It must be more maneuverable and capable of precise placement and adjustment of this balloon in a vascular location and, thus, a great deal more flexible. This stem portion needs to be able to transmit rotational torque, as well as being capable of being advanced over a guidewire for location at a stenoses of interest. The sidewall of the distal stem section typically is also fabricated of a relatively inert polymer material having a low coefficient of friction which may surround a reinforcing coil core or, less likely, a reinforcing braid of reduced stiffness. The relative hardness of the distal stem section is typically from about 45 to as high as 72 Durometer, but more typically about 50 Durometer (D Shore Scale).

The two sections of contrasting construction and purposes are typically joined by being consecutively bonded in the presence of an overlapping transition zone. Kinking and other operational problems associated with the abrupt change, however, have made use quite tedious for the physician. The transition zone would advantageously be characterized by physical properties intermediate those of the proximal shaft and the distal stem. To date, however, although progress has been made in the provision of trouble-free transition sections, the problems associated with the contrast in stiffness and other maneuverability characteristics between the proximal shaft and the distal working stem section have not been solved and kinking and other problems still occur making practical use of the system more difficult.

Accordingly, it is a primary object of the present invention to provide a smooth, kink-resistant transition zone for joining a proximal shaft in a distal working stem in a dedicated vascular catheter.

It is another object of the present invention to create a smooth, kink-resistant transition from braided polyimide to a polyethylene stem on an over the wire dilatation catheter system.

Yet another object of the invention is to provide a method of joining catheter sections of diverse stiffness in a manner that creates a smooth, kink-resistant transition.

Other objects and advantages of the invention will become apparent to those skilled in the art upon familiarization with the specification, drawings and appended claims contained herein.

SUMMARY OF THE INVENTION

In accordance with the present invention there is provided an improved catheter construction and method dealing with the creation of a smooth kink-resistant transitional zone joining small diameter polymeric tubes and reinforced polymeric tubes of varying hardness and flexibility. The intermediate transitional zone or section concept of the invention contemplates a composite segment of common outside diameter but relatively lower hardness Durometer than the proximal shaft, but higher than that of the distal stem connecting the distal end of a rather stiff proximal catheter shaft with a relatively more flexible distal working or stem section which typically carries a device to be deployed vascularly with some precision such as a dilatation balloon. The concept further contemplates continuity of the internal lumens connecting the sections joined, as well as external continuity of the common outside diameter if required.

While generally a single transition segment of intermediate hardness and stiffness will suffice to modify the sharp contrast between the stiffness of the proximal shaft and the relatively flexible distal stem, additional intermediate segments which reduce the hardness or stiffness in several steps are clearly contemplated. As used herein, the term "shaft" is defined as the proximal relatively more rigid portion of the catheter device or system and the term "stem" is used to denote the relatively more flexible distal portion that normally carries the dilatation or other device to accomplish the procedure of interest.

The detailed description describes an embodiment in which a stainless steel coil or braid-reinforced polyimide, or the like, tubular catheter shaft is joined to a polyolefinn, normally polyethylene distal stem section utilizing a short segment including a composite construction polyolefin collar or sleeve overlapping both, and which replaces the final segment of the polyimide outer layer above the braid is one illustrative embodiment.

The method of the invention for joining the diverse hardness materials begins with treating the outer surface of a short segment (about 1.5 in. or about 38 mm in length) at the distal end of the shaft with a solvent material to strip and remove the outer and inner coating of polyimide or other polymer material and expose the stainless steel reinforcing braid. This may be accomplished on polyimide using a 10% (volume) solution of caustic material such as potassium hydroxide (KOH) or sodium hydroxide (NaOH). The stripped or stepped down segment is then stretched over a 0.030–0.031 in. (0.762–0.987 mm) mandrel sized according to the internal diameter and configuration of the shaft including provision, as necessary, for a plurality of separated continuous internal lumens. Once the exposed braid is stretched over the mandrel, it is heated using a micro welder to anneal the material and the end is trimmed to the desired length of exposed braid by roll cutting using a sharp instrument. As stated, typically 3.8 cm (1.5 in.) of exposed material is allowed.

A short coupling segment or sleeve of compatible polymer material of intermediate hardness such as a linear, low density polyethylene such as Dowlex 2038 polyethylene (PE) (Dow) is applied so as to slide over the exposed braid. The length of the intermediate coupling segment is such that it overhangs the distal end of the non-stripped polyimide proximal shaft by about 0.15 in. (0.46 cm) and overlaps the braid-reinforced segment by approximately 1.5 in. (38 mm). This portion of the distal stem segment or sleeve coupling extending over the stripped or stepped down distal end of the proximal shaft is necked down at a temperature of about 225° F. (107° C.) to assume an outside diameter less than that of the remainder of the proximal shaft. The overhanging portion is also reduced and an additional sleeve or collar of typically harder, higher density polyethylene material such as 8320 PE (Quantum) is applied as an outer layer over the necked down section of 2038 PE to provide a smooth transition between the polyimide and the 8320 polyethylene at the outer surface. The outside diameter of the 8320 PE collar is designed to match the tube outside diameter. In this manner, the second sleeve layer is slid over the first and located over the braided area.

Finally, a layer of fluorinated ethylene propylene (FEP) shrink tubing is applied over the second coupling on the necked down area and the entire material is re-heated to about 200° C. causing the 2038 PE polymer to flow into the braids and the outer 8320 PE layer also to flow and bond to the 2038 PE layer and the polyimide. In this manner, a stable collar of intermediate hardness and flexibilities is produced with (or transition zone) which to bond over the flexible distal stem material which is also 2038 polyethylene which, of course, readily bonds to the 2038 transition collar. The shrink tubing is then removed and discarded. Of course, the distal stem matches, bonds to and continues the internal catheter lumens of the proximal shaft as required.

The process effects creation of a smooth, kink-resistant transition phase from the relatively stiff braid-reinforced polyamide proximal shaft to the relatively flexible 2038 polyethylene stem that enables relatively trouble-free operation of the system, including arterial system navigation and the accurate deployment of the balloon dilatational catheter for stenoses suppression. The preferred or detailed embodiment describes a stainless steel braid reinforced polyimide proximal shaft in combination with a 2038 polyethylene distal stem section. Typically, the polyimide shaft has a Durometer or hardness from about 70 to 80 Durometer (D Shore Scale). The 2038 polyethylene distal stem section may be coil rather than braid reinforced and typically will have a Durometer as low as 45, but not exceeding 65 (D Shore Scale). In addition, other materials can be utilized for both, the chosen materials being typical of those employed, but not limiting and only intended to be illustrative of the principles underlying the invention.

BRIEF DESCRIPTION OF THE DRAWINGS

In the drawings wherein like reference numerals depict like parts throughout the same.

DETAILED DESCRIPTION

In accordance with concepts of the invention, improvements are provided in catheter tube construction involving use of proximate sections having different physical characteristics, primarily differences in hardnesses and flexibilities. The invention can be applied generally to achieve a smooth transition and relatively kink-free operation between dissimilar sections. In this manner, the performance of devices of the class is improved particularly with regard to interfaces between catheter lengths or sections characterized by abrupt changes in hardness and flexibility. This is particularly exemplified by the connection of relatively stiff (nominally 72–80 Durometer (D Shore Scale), a proximal dilatation catheter shaft and the relatively flexible (Durometer 45–70, D Shore Scale), distal stem carrying the dilatation balloon device. The improved transition concept is particularly beneficial with respect to the operation of devices of the class in vascular navigation and dilatation device placement. The following detailed embodiment exemplifies without limitation application of the principals of the invention both from the standpoint of type of catheters including bitumen configuration and materials of construction of the shaft, stem and transition.

Figure 1A:
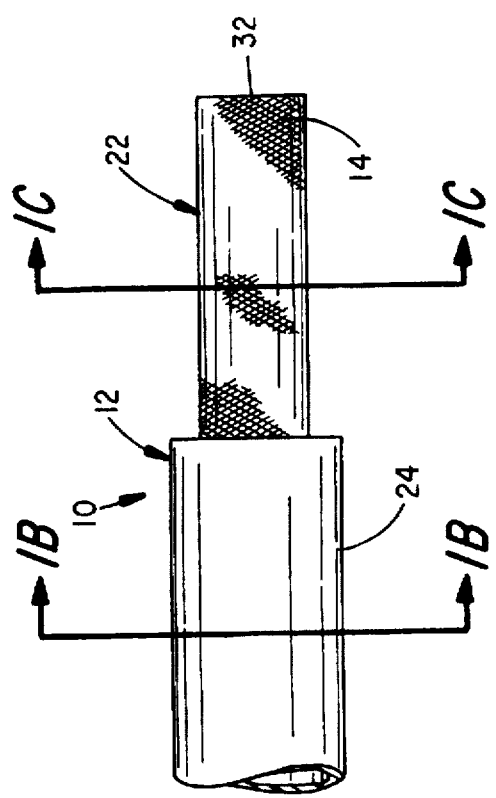
FIG. 1A is a schematic view of a broken fragmentary segment of a proximal catheter shaft with the polyimide outer layer removed exposing the reinforcing braid in accordance with the process of the present invention.
Figure 1B:
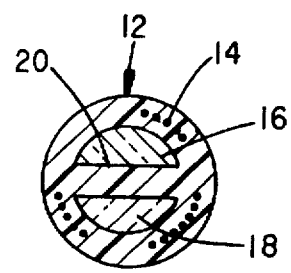
FIG. 1B and 1C are representative cross sectional views of the catheter shaft of FIG. 1A indicates by sectional lines B—B and C—C, respectively, of FIG. 1A showing a bilumen construction.
Figure 1C:
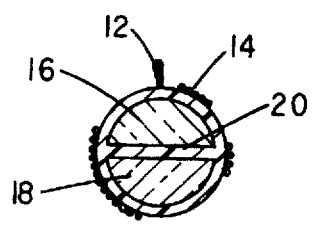

The figures depict a method of joining catheter sections of dissimilar hardness and flexibility. FIGS. 1A–1C illustrating a fragmentary distal end segment of a proximal shaft to be joined to a distal stem (shown fragmentally in FIG. 6 and 7) carrying a dilatation device or the like. FIGS. 1A–5 depict the processing of the proximal shaft end and FIGS. 6 and 7 include connection to the stem.

FIGS. 1A–1C depict a broken distal fragmental segment 10 representing schematically the distal end of a relatively stiff main dilatation catheter shaft (not shown) to be joined to a distal stem by the instant process. The segment includes a polymeric tube 12 containing an intermediate braided reinforcing layer 14 sandwiched between layers of polymer material, nominally woven of very fine stainless steel wire. The tube 12 is shown in FIGS. 1B and 1C as being divided into a pair of parallel internal lumens 16 and 18 separated by a common internal membrane 20, also of a polymer common with the outer tube wall 12, classically a polyimide.

The process of the invention includes adding a short transition zone to the distal end of a relatively stiff proximal catheter shaft and thereafter joining it with the proximal end of a relatively flexible continuing stem section carrying a device for implementing a particular procedure. The implementation of the transition zone begins with the preparation of the distal end of the shaft.

In FIG. 1A, a length of the right side or distal end of the tube 12 at 22 has been treated on its outer surface by a solvent material for a sufficient time to selectively remove the outer polymer layer or layers overlaying the stainless steel braid 14 and thereby exposing a short segment of the braid. Materials for removing the polyimide layer include strong base materials such as KOH and NaOH about 10% by volume in $H_2O$. The left or proximal portion of the fragmental section at 24 remains intact as does the remainder of the continuous shaft.

The solvent material is then removed by washing and the segment is stretched over a mandrel of congruent size and shape to accommodate where necessary, the tube and, a pattern of internal lumens of the tube 12 particularly with respect to the segment 22. The mandrel is heated to about 225° F. (110° C.) to stabilize the stripped or stepped down section for application of a transition collar or sleeve. If necessary, the length of the stripped section 22 is adjusted as is the tension in the braided layer which may be retained, unchanged or severed parallel to the tube depending on the application.

Figure 2:
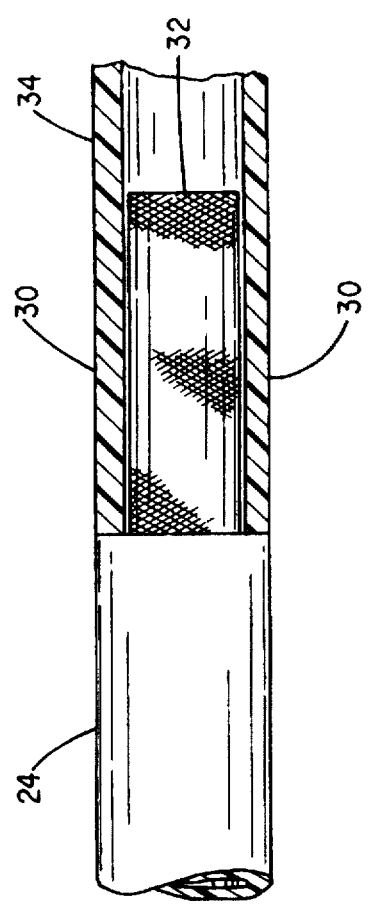
FIG. 2 is similar to FIG. 1A with an inner transition sleeve or inner collar applied over the exposed braid.

Thereafter, as shown in FIG. 2, a first or inner, relatively narrow collar or transitional tubing sleeve 30 rather wider than the stripped section 22 is shown slid over the stripped section and extending beyond the end 32 of the section 22 for a distance at 34. The length of the stripped section is typically 1.5 in. (38 mm) and the typical extension or overhang at the distal end of the stripped segment 22 is about 0.15 in. (0.46 cm). The collar or sleeve 30 is applied with the material at a temperature of approximately 225° F. (107° C.). The sleeve 30 typically has an outside diameter equal to that of the tube 12.

Figure 3:
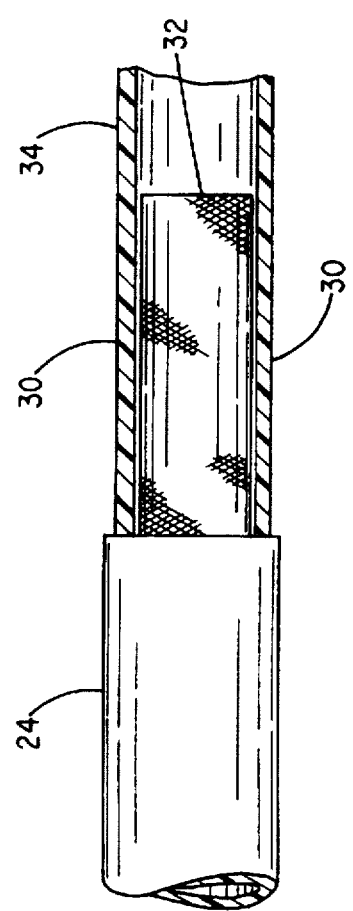
FIG. 3 is a view similar to FIG. 2 with outside diameter of the portion of the inner sleeve overlaying the braid necked down.

As illustrated in FIG. 3, the inner sleeve 30 overlaying and extending beyond the stepped down section 22 of the tube segment 12 is then subjected to a thickness reduction step. This is typically accomplished by drawing or pulling through a heated die at about 225° F. (107° C.). The reduction of the tube 30 may also be accomplished using a heat shrinking step if desired in conjunction with the application of an overlaying segment of shrink tubing as discussed below in relation to the combined layers. This step also results in a partial melting of the inner collar 30 into the braid or coil 14 in the segment 22.

Figure 4:
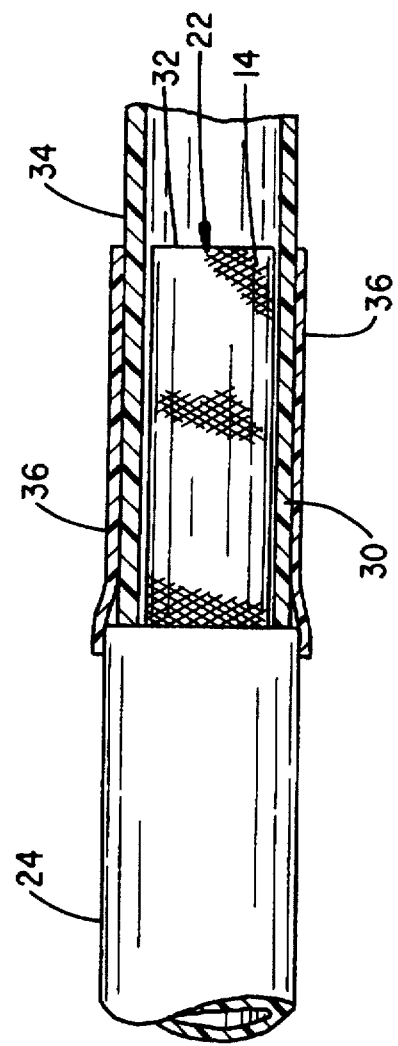
FIG. 4 is a view similar to FIG. 3 with a second or outer collar section applied over the area of reduced diameter of the inner collar.
Figure 5:
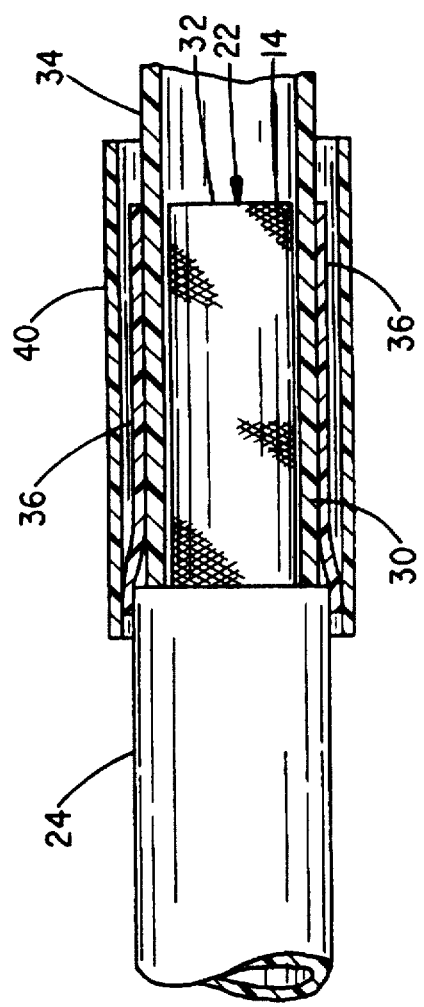
FIG. 5 is a view similar to FIG. 4 with a layer of shrink tube located over the inner and outer collar above the exposed braided area of the shaft.

As shown in FIG. 4, a second or outer collar or sleeve 36 is next slipped over the inner sleeve 30 covering the portion of reduced outside diameter proximal the segment 34. The outer sleeve 36 is normally of a thickness such that when combined with the inner sleeve 30 will provide a composite smooth tubular coupling on segment 22 to blend with the outside diameter of the tubular catheter shaft at 24.

Next, a thin section of the appropriate size shrink tubing (shown at 40 in FIG. 5) is slipped over the outer transition sleeve. The shrink tubing contracts with considerable force when heated. The end of the proximal shaft of tubular segment 10 is again heated on the mandrel inner sleeve 30 is caused to soften and the heat and the force of the shrink tube induce it to blend into the reinforcing braid. Likewise the outer collar or sleeve is compressed to combine with the inner collar or sleeve to form therewith a continuous composite outside casing to the distal end of the proximal shaft. The extended or overhanging portion 34 of inner sleeve 30 remains intact on the mandrel. In this manner, a composite shell is provided blending the flanking section 34 and with tube 24 to provide a smooth transitional area as illustrated at 42 in FIG. 6.

The temperature of the forming step is approximately 200° C. for about 1-3 minutes. Thereafter, the shrink tubing is slit and removed leaving the transition area intact.

Figure 6:
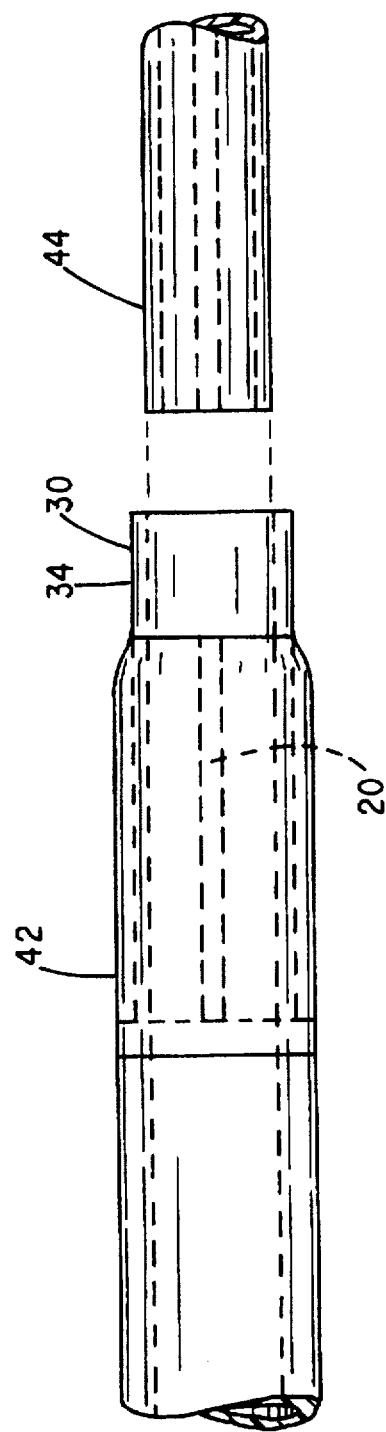
FIG. 6 depicts the finished transition section after heat shrinking ready to receive the distal stem and a broken fragmentary distal stem to be received in an overlapped joint fashion.
Figure 7:
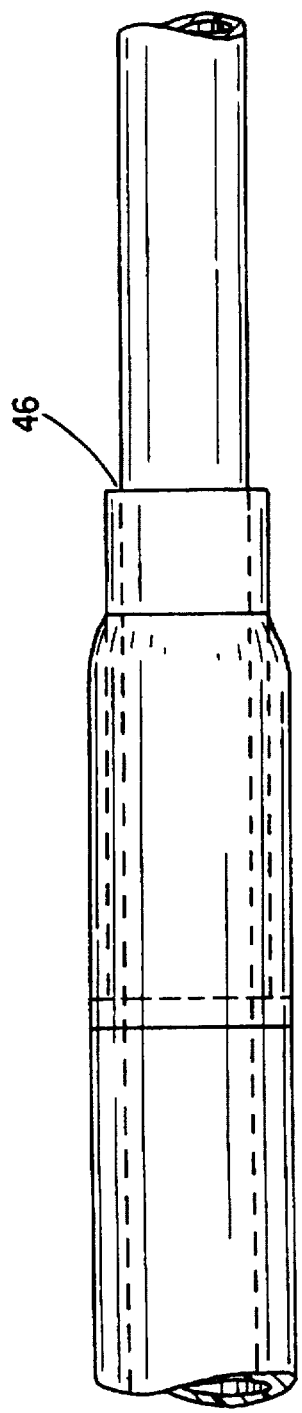
FIG. 7 depicts the fragments of FIG. 6 joined together in overlapping fashion.

Also seen in FIG. 6 is a proximal fragment of a distal stem member shown broken at 44 designed to connect to the distal end of the proximal shaft. The member 44 is pictured to fit in the portion 34 of the member 30 in a slip fit or overlapping joint 46 as shown assembled in FIG. 7. That joint can be a melt bonded or adhesively connected. Also other type joints including butt joints can be employed to join 34 and 44. The connection and continuity of the internal lumens 16 and 18 is also preserved in the segment 44.

With respect to the materials of construction, a wide variety of choices is possible depending on the application. The inner or lower collar or sleeve, as well as the upper or outer sleeve and distal stem are typically of a polyolefin material and commonly polyethylene (PE). The inner or lower sleeve preferably is of the same polyolefin material as the stem 44 which is more flexible than the dual sleeve sector which, in turn, is more flexible than the proximal shaft 26. The stem 44 may also be braid or coil reinforced. The preferred material of the proximal shaft 26 is a polyimide such as manufactured by Micro Lumen. The inner sleeve 30, and so the extension segment 34, can be a relatively flexible, relatively low density material, preferably linear low density polyethylene such as Dowlex 2038 manufactured by Dow Chemical Company of Midland, Mich. (Dowlex is a trademark of the Dow Chemical Company) and the outer or upper sleeve a slightly harder higher density material preferably a high density polyethylene such as PETROTHENE LB 8320-00 sheet and profile extrusion and thermaforming grade obtained from Quantum Chemical Company of Cincinnati, Ohio (PETROTHENE is a trademark of Quantum Chemical Company).

An outer or overlay sleeve made of 8320 PE has a normal wall thickness of approximately 0.001–0.005 in. The nominal hardness of the unstripped polyimide proximal shaft, at 26 is between 72 and 80 Durometer (D Shore Scale) and the nominal hardness of the transitionary including the double collar system above the braided area is approximately 60–75 Durometer (D Shore Scale) and that of the 2038 polymer connecting section 34 with the stem section 44 is approximately 50–72 Durometer (D Shore Scale). The stem section of a dilatation balloon catheter of the class illustrated is normally between about 45 and 70 Durometer (D Shore Scale) and is normally about 50 Durometer (D Shore Scale).

As can be seen from the process of the invention, the transition sleeves can be of any type of material compatible with the remainder of the proximal shaft and the stem to be distally attached as long as it provides a low friction, relatively smooth transition having the desired intermediate hardness and flexibility. It is further contemplated with respect to the invention that such that a transition between a highly flexible distal stem and a fairly rigid proximal shaft can be carried out utilizing more than one transitional step or area fabricated in accordance with the invention.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A method of joining proximal shaft and distal stem sections of a tubular catheter device wherein said proximal shaft and said distal stem have substantially dissimilar flexibilities comprising the steps of:

(a) removing an outer layer of tubular sidewall from a short distal segment at a distal end of the proximal shaft to produce a stepped down distal end thereon;

(b) fitting a short inner sleeve member over the stepped down distal end of said shaft, said inner sleeve member extending beyond said distal end forming a sleeve extension;

(c) reducing the outside diameter of said inner sleeve by drawing through a heated die;

(d) fitting an outer sleeve member over said inner sleeve member;

(e) applying a heat shrinkable material over said outer sleeve member and applying sufficient heat to achieve a composite transition section at said stepped down end of said shaft including said inner and said outer sleeves, said composite transition section having a flexibility greater than that of said shaft;

(f) removing said heat shrinkable material; and (g) attaching a stem section to said sleeve extension.

2. The method of claim 1 wherein said composite transition section has the same outside diameter as said shaft.

3. The method of claim 1 wherein said step of attaching said stem section includes fitting said stem section inside said sleeve extension of said inner sleeve.

4. The method of claim 1 wherein said composite transition section has a greater flexibility than said shaft.

5. The method of claim 4 wherein said stem section has a greater flexibility than said transition section.

6. The method of claim 1 wherein said inner sleeve is more flexible than said outer sleeve.

7. The method of claim 5 wherein said inner sleeve is more flexible than said outer sleeve.

8. The method of claim 4 wherein said shaft comprises polyimide, said inner sleeve is low density polyethylene and said outer sleeve is high density polyethylene.

9. The method of claim 6 wherein said stem comprises the same material as said inner sleeve.

10. The method of claim 8 wherein said stem comprises a low density polyethylene material.

* * * * *